United States Patent

Kim et al.

Patent Number: 5,457,210
Date of Patent: Oct. 10, 1995

[54] INTERMEDIATES FOR THE PREPARATION OF PYRAZOLOAZOLE PHOTOGRAPHIC COUPLERS, PROCESSES OF MAKING AND USING THEM

[75] Inventors: Chang K. Kim, Pittsford; Joan C. Potenza, Rush; Francesco DeBellis, Rochester; David Hoke, Rochester; Robert F. Romanet, Rochester, all of N.Y.

[73] Assignee: Eastman Kodak Company, Rochester, N.Y.

[21] Appl. No.: 231,602

[22] Filed: Apr. 22, 1994

[51] Int. Cl.⁶ .................................................. C07D 487/04
[52] U.S. Cl. ........................................................ 548/262.4
[58] Field of Search ........................... 548/262.4; 514/383

[56] References Cited

U.S. PATENT DOCUMENTS

| | | | |
|---|---|---|---|
| 3,725,067 | 4/1973 | Bailey et al. | 96/56.5 |
| 4,254,132 | 3/1981 | Krämer et al. | 424/269 |
| 5,055,586 | 10/1991 | Kim et al. | 548/262.4 |

FOREIGN PATENT DOCUMENTS

0476659  3/1992  European Pat. Off. .

OTHER PUBLICATIONS

Elnagdi et al., J. Het. Chem, 14, 227–30 (1977) Apr.
Bailey, J. Chem. Soc. Perk. I 2047–52, (1977) (5).
Farag et al., J. Het. Chem, 24, 1341–44, (1987) Sep.–Oct.

Primary Examiner—Johann Richter
Assistant Examiner—Laura L. Stockton
Attorney, Agent, or Firm—Joshua G. Levitt

[57] ABSTRACT

There are described intermediates for the preparation of known pyrazoloazole photographic magenta dye forming couplers and processes for making and using these intermediates. The intermediates are low molecular weight compounds represented by the structure:

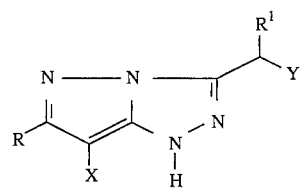

wherein:
R, X, $R^1$ and Y are defined herein.

The process for making these intermediates involves diazotizing a 5-amino-1H-pyrazole to produce a 5-diazo-1H-pyrazole, then condensing the diazotized product with an active methine or methylene compound having a pKa of 14 or less to produce a substituted hydrazone and then subjecting the hydrazone to cyclization and reduction, in either order.

1 Claim, No Drawings

INTERMEDIATES FOR THE PREPARATION OF PYRAZOLOAZOLE PHOTOGRAPHIC COUPLERS, PROCESSES OF MAKING AND USING THEM

FIELD OF THE INVENTION

This invention relates to novel intermediates for the preparation of pyrazolotriazole photographic coupler compounds, to methods of making the intermediates, and to methods of using the intermediates to make photographic couplers. In a particular aspect it relates to intermediates for the preparation of 1-H-pyrazolo[5,1-c]-1,2,4-triazoles.

BACKGROUND OF THE INVENTION

Pyrazoloazoles have been known to be useful as magenta dye forming couplers since they were described as being useful for that purpose in Bailey et al. U.S. Pat. No. 3,725,067 issued Apr. 3, 1973. Known processes for preparing these coupler compounds are described, for example, in the Bailey '067 patent, in U.S. Pat. No. 5,055,586 and in Sato, European Published Application 0 476 659, published Mar. 25, 1992. Processes for preparing specific pyrazoloazole compounds are described in Bailey, J. Chem. Soc. Perk. I 2047–52, (1977); Elnagdi et al., J. Het. Chem, 14, 227–30, (1977); and in Farag et al., J. Het. Chem, 24, 1341–44, (1987).

The known processes for preparing pyrazoloazole magenta dye forming couplers add functionality that defines the desired coupler compound early in the synthesis. This results in a lack of generality of the process and the need to make different intermediates for different end coupler compounds.

Furthermore, the known processes for preparing these magenta dye forming couplers involve the use of sulfur-containing intermediates which present a danger of residual sulfur in the compound. Sulfur is a known contaminant for photographic systems.

It would be desirable to have intermediates that could be used to make a variety of end coupler compounds. It also would be desirable to have such intermediates which can be prepared by synthetic routes which do not involve sulfur containing compounds.

We have found such intermediates, methods of making them and methods of using them to make pyrazoloazole photographic couplers.

SUMMARY OF THE INVENTION

In one aspect this invention relates to novel intermediates for the preparation of 1-H-pyrazolo[5,1-c] -1,2,4-triazole magenta dye forming couplers, the intermediates having the following structural formula:

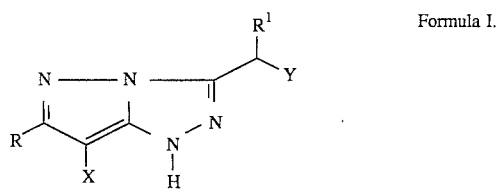

Formula I.

wherein:
R is an alkyl, acyl, aryl or heterocyclyl group, linked to the ring directly or through a hetero atom;

X is hydrogen, a precursor of a coupling-off group, or a coupling-off group;

$R^1$ is hydrogen, or an alkyl, aryl or heterocyclyl group; and

Y is a leaving group which can be replaced by a nucleophilic replacement or an elimination/addition reaction, the intermediate being of such size and bulk that it can wander through the gelatin containing layers of a silver halide photographic element.

In another aspect this invention relates to a method of making intermediates of Formula I, the method comprising the steps of:

(1) diazotizing a 5-amino-1H-pyrazole in the presence of an acidic nitrite salt or ester to produce a 5-diazo-1H-pyrazole;

(2) condensing the diazotized product in the presence of an active methine or methylene compound having a pKa of 14 or less to produce a substituted hydrazone compound;

(3) subjecting the hydrazone product to cyclization and reduction, in either order, to produce the intermediate compound of Formula I.

In yet another aspect this invention relates to a method of making 1-H-pyrazolo[5,1-c]-1,2,4-triazole magenta dye forming couplers, the method comprising the steps of 1) providing an intermediate of Formula I;

2) replacing Y with a coupler ballast group by means of a nucleophilic replacement reaction or an elimination-addition reaction.

The compounds of Formula I provide a common intermediate from which a variety of 1-H-pyrazolo[5,1-c] -1,2, 4-triazole magenta dye forming couplers can be prepared. The intermediates can be synthesized using simple steps which do not involve reactions with sulfur containing compounds that leave sulfur contaminants.

Other advantages of the present invention is that the synthetic route to the common intermediate avoids the need to isolate toxic hydrazino compounds, which most prior syntheses have used. Reasons for preferring the common intermediates of this invention to other compounds from which ballasted pyrazoloazole couplers have been synthesized, relate to the fact that the functionalities that define the end coupler are not added until late in the synthesis of the coupler. This permits use of a relatively small inventory of intermediate compounds, thus reducing cost. It also means that the intermediate compound can be of relatively low molecular weight, thus reducing the weight and volume of material handled and reducing cost. Moreover, the syntheses permits many different examples to be produced quickly, allowing for rapid evaluation of new couplers and the ability to build up a large storehouse of data for structure-activity correlation.

DETAILED DESCRIPTION OF THE INVENTION

The novel intermediates of Formula I are similar to compounds that have been described as dye forming coupler compounds, but differ from them in that the present compounds are not of sufficient bulk to not wander through the layers of a photographic element. Thus, if an intermediate of this invention were incorporated in one of the gelatin emulsion layers of a silver halide photographic element, it would wander from that layer to other layers, where its presence would not be desired. The ability of a compound not to wander is a function of the bulk of the compound, which relates not only to molecular weight, but also to the stereoconfiguration of the molecule and its ionic properties.

Generally, intermediates of this invention have a molecular weight of less than 500, preferably a molecular weight in the range of 200 to 400.

In Formula I, the group represented by R can be any of the groups found in this position on the corresponding coupler, or precursors of such groups. Representative R groups include alkyl, aryl, heterocyclyl, alkoxy, aryloxy, amido, amino, alkylthio, arylthio, alkyloxysulfonyl, aryloxysulfonyl, alkylsulfonyl, arylsulfonyl, and the like. The alkyl portion of the above groups contains from 1 to 12 carbon atoms and includes cycloalkyl, aralkyl and heteroalkyl, such as methyl, ethyl, propyl, isopropyl, butyl, isobutyl, t-butyl, pentyl, hexyl, heptyl, nonyl, decyl, undecyl, dodecyl, cyclopropyl, cyclobutyl, cyclopentyl, cyclohexyl, benzyl, phenethyl, phenylpropyl, phenylbutyl and the like, which can be unsubstituted or substituted with noninterfering groups. The aryl portion of the above groups contains 6 to 12 carbon atoms and includes alkaryl and heteroaryl, such as phenyl, halophenyl, nitrophenyl, aminophenyl, carboxyphenyl, methoxycarbonylphenyl, hydroxyphenyl, ethoxyphenyl and the like, which can be further substituted with noninterfering substituents. The heterocyclic portion of the above groups contains 5 to 12 ring atoms and includes heterocycles, such as pyrazolo, pyrrole, oxazole, thiazole, pyridine, furan, thiopene, hydantion, and the like, which can be further substituted with noninterfering substituents.

Preferred R groups are methyl, ethyl, isopropyl, t-butyl, methoxy, ethoxy, phenyl, methylphenyl, chlorophenyl, nitrophenyl, methoxyphenyl and t-butylamido.

In Formula I, the group represented by X can be hydrogen, or any of the coupling-off groups known in the photographic art to be replacable by oxidized color developing agent during photographic processing, or a precursor of such a coupling-off group. Representative X groups include hydrogen, halogen, expecially chloro, alkoxy, aryloxy, alkylthio, arylthio, heteroaryl and the like. The alkyl and aryl portions of these groups are as defined above for R. Particularly preferred X groups are hydrogen and halogen, such as chloro, aryloxy, such as phenoxy and arylthio, such as phenylthio.

In Formula I, the group represented by $R^1$ can be hydrogen, alkyl, aryl, and heterocyclic, as defined above for R. Preferred $R^1$ groups are alkyl of 1 to 4 carbon atoms, such as methyl, ethyl, isopropyl, isobutyl, and t-butyl and aryl of 6 to 12 carbon atoms, such as phenyl, chlorophenyl, methylphenyl, methoxyphenyl and nitrophenyl. Particularly preferred $R^1$ groups are methyl and phenyl.

In Formula I, the group represented by Y can be halogen, hydroxy, amino, alkoxy, aryloxy, acyloxy, alkylsulfonyloxy and arylsulfonyloxy, all of which can be substituted or unsubstituted. The alkyl and aryl portions of these groups are as defined above for R. Preferred Y groups are acyloxy, aryloxy, alkoxy, halogen, arylsulfonyloxy, and alkylsulfonyloxy. Particularly preferred are acetoxy and phenoxy.

Preferred intermediates have the structure of Formula I, wherein: R is methyl, isopropyl, t-butyl, ethoxy, t-butylamido and phenyl; X is chloro, phenoxy, phenylthio, 1-H-pyrazolyl and 1-H-hydantoyl; $R^1$ is methyl, ethyl, isopropyl, and phenyl; and Y is acetoxy, phenoxy, hydroxy, methoxy, methanesulfonyloxy, and p-toluenesulfonyloxy.

Representative intermediate of Formula I are shown in Table I below:

TABLE I

FORMULA I

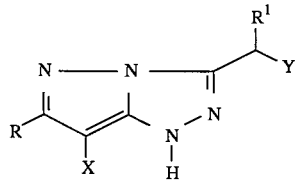

| Ex. | R | $R^1$ | X | Y |
|---|---|---|---|---|
| 1 | $CH_3$ | $CH_3$ | H | $OCOCH_3$ |
| 2 | $CH_3$ | $CH_3$ | Cl | $OCOCH_3$ |
| 3 | $CH_3$ | $CH_3$ | H | Cl |
| 4 | $CH_3$ | $CH_3$ | Cl | Cl |
| 5 | $CH_3$ | $CH_3$ | Cl | $OCH_3$ |
| 6 | $CH_3$ | $CH_3$ | O—Ph | $OCOCH_3$ |
| 7 | $CH_3$ | $CH_3$ | O—C$_6$H$_4$—$CH_3$ | $OSO_2CH_3$ |
| 8 | $CH_3$ | $CH_3$ | O—C$_6$H$_4$—$CO_2CH_3$ | $OCOCH_3$ |
| 9 | $CH_3$ | $CH_3$ | O—C$_6$H$_4$—$SO_2CH_3$ | $OCOCH_3$ |

TABLE I-continued

FORMULA I

[Structure: pyrazolotriazole with substituents R, X, R¹, Y]

| Ex. | R | R¹ | X | Y |
|---|---|---|---|---|
| 10 | CH₃ | CH₃ | 4-(2-benzyloxyphenylsulfonyl)phenoxy (O-C₆H₄-SO₂-C₆H₄-OCH₂C₆H₅) | OCOCH₃ |
| 11 | CH₃ | CH₃ | OCH₃ | OCOCH₃ |
| 12 | CH₃ | CH₃ | 1-methylpyrazol-2-yl | OCOCH₃ |
| 13 | CH₃ | CH₃ | 3-methyl-1-benzylhydantoin-N-CH₂- | OCOCH₃ |
| 14 | CH₃ | CH(CH₃)₂ | Cl | OCOCH₃ |
| 15 | CH₃ | (CH₂)₃CH₃ | Cl | OCOCH₃ |
| 16 | CH₃ | (CH₂)₃CO₂H | Cl | OCOCH₃ |
| 17 | CH₃ | Ph | H | OCOCH₃ |
| 18 | CH₃ | Ph | Cl | OCOCH₃ |
| 19 | CH₃ | Ph | H | Cl |
| 20 | CH₃ | Ph | Cl | Cl |
| 21 | CH₃ | Ph | Cl | OCH₃ |
| 22 | CH₃ | Ph | OPh | OCOCH₃ |
| 23 | CH₃ | Ph | O-C₆H₄-CH₃ (4-methylphenoxy) | OCOCH₃ |
| 24 | CH₃ | Ph | O-C₆H₄-CO₂CH₃ | OCOCH₃ |
| 25 | CH₃ | Ph | O-C₆H₄-SO₂CH₃ | OCOCH₃ |
| 26 | CH₃ | Ph | 4-(2-benzyloxyphenylsulfonyl)phenoxy (O-C₆H₄-SO₂-C₆H₄-OCH₂C₆H₅) | OCOCH₃ |
| 27 | CH₃ | Ph | OCH₃ | OCOCH₃ |
| 28 | CH₃ | Ph | 1-methylpyrazol-2-yl | OCOCH₃ |

TABLE I-continued

FORMULA I $$\text{Pyrazolo-triazole structure with substituents R, R}^1\text{, X, Y}$$

| Ex. | R | R¹ | X | Y |
|---|---|---|---|---|
| 29 | CH₃ | Ph | 1,3-disubstituted hydantoin (N-CH₃, N-CH₂C₆H₅, with CH₂ linker via C=O) | OCOCH₃ |
| 30 | CH₃ | 3-NO₂-C₆H₄ | Cl | OSO₂CH₃ |
| 31 | CH₃ | 4-Cl-C₆H₄ | Cl | OCOCH₃ |
| 32 | CH₃ | 4-OCH₃-C₆H₄ | Cl | OCOCH₃ |
| 33 | CH₃ | 4-CH₃-C₆H₄ | O-(4-CH₃-C₆H₄) | OSO₂-(4-CH₃-C₆H₄) |
| 34 | CH(CH₃)₂ | CH₃ | Cl | OCOCH₃ |
| 35 | CH(CH₃)₂ | Ph | Cl | OCOCH₃ |
| 36 | C(CH₃)₃ | CH₃ | Cl | OCOCH₃ |
| 37 | C(CH₃)₃ | Ph | Cl | OCOCH₃ |
| 38 | OCH₂CH₃ | CH₃ | Cl | OCOCH₃ |
| 39 | OCH₂CH₃ | Ph | Cl | OCOCH₃ |
| 40 | NHCOC(CH₃)₃ | CH₃ | Cl | OCOCH₃ |
| 41 | NHCOC(CH₃)₃ | Ph | Cl | OCOCH₃ |
| 42 | Ph | CH₃ | Cl | OCOCH₃ |
| 43 | Ph | CH₃ | Cl | Cl |
| 44 | Ph | CH₃ | Cl | OCH₃ |
| 45 | Ph | CH₃ | Cl | OSO₂CH₃ |
| 46 | Ph | Ph | Cl | OSO₂-(4-CH₃-C₆H₄) |
| 47 | Ph | Ph | Cl | OCOCH₃ |

TABLE I-continued

FORMULA I

[Structure: pyrazole ring with substituents R, R¹, X, Y]

| Ex. | R | R¹ | X | Y |
|---|---|---|---|---|
| 48 | -C₆H₄-Cl | CH₃ | Cl | OSO₂-C₆H₄-CH₃ |
| 49 | -C₆H₄-Cl | Ph | Cl | OCOCH₃ |
| 50 | -C₆H₄-NO₂ | CH₃ | Cl | OCOCH₃ |
| 51 | -C₆H₄-NO₂ | Ph | Cl | OCOCH₃ |
| 52 | -C₆H₄-OCH₃ | CH₃ | Cl | OCOCH₃ |
| 53 | -C₆H₄-OCH₃ | Ph | Cl | OCOCH₃ |
| 54 | -C₆H₄-CH₃ | CH₃ | Cl | OCOCH₃ |
| 55 | -C₆H₄-CH₃ | Ph | Cl | OCOCH₃ |

The common intermediates of the invention can be synthesized in a number of different ways. As indicated above, a preferred synthetic route to the common intermediate, which is a part of this invention, involve diazotizing a 5-amino-1H-pyrazole to produce a 5-diazo-1H-pyrazole, then condensing the diazotized product with an active methine or methylene compound having a pKa of 14 or less to produce a substituted hydrazone and then subjecting the hydrazone to cyclization and reduction, in either order, to produce the common intermediate compound of Formula I. In a preferred aspect, the product of the cyclization/reduction steps is acylated to activate the side chain methine group in the 3 position on the ring.

Diazotization of the 5-amino-1H-pyrazole is carried out with an acidic nitrite salt or ester in a water miscible organic solvent at a temperature sufficiently low to avoid decomposition of the diazo product. The 5-amino-1H-pyrazole can be substituted with groups that will lead to the desired substitution in the common intermediate. Thus, it can contain in the 2 position an alkyl, aryl or heterocyclyl group as defined above for R in Formula I, or a precursor of such a group. The acidic environment is provided by a mineral acid, such a hydrochloric acid or sulfuric acid and the nitrite preferably is a salt or ester, such as sodium nitrite, butyl nitrite or amyl nitrite. Suitable water miscible solvents include alcohols, such as isopropyl alcohol, ethyl alcohol, methyl alcohol, acetonitrile, acetone and tetrahydrofuran. Suitable reaction temperatures are below 25° C., preferably from −10° C. to +20° C. The reaction proceeds to completion in less than an hour, typically in about 30 minutes.

Condensation of the diazonium salt product with an active methylene compound occurs in a water miscible solvent, as in the diazotization reaction, at a temperature below 25° C. The active methylene compound is a carbon atom to which is attached 2 or more electron withdrawing groups, at least one of which is a carbonyl group. Other suitable electron withdrawing groups include nitro, nitrile and ammonium. Preferred active methylene compounds include 3-chloro-2,4-pentanedione, and 1-(2-oxo-phenylethyl)-pyridinium chloride. This condensation reaction is known as the Japp-Klingman reaction and is described in additional detail in Organic Reactions, Vol. X; pp.143–179; Robert E. Krieger Publishing Co; Huntington, N.Y.; 1975. After the condensation reaction, the product preferably is neutralized with an inorganic salt of a weak acid, such as sodium acetate.

The hydrazone product resulting from the condensation reaction can be collected by procedures common in the art. It then is reduced and cyclized, in either order, in an aprotic polar solvent to yield an intermediate of Formula I above. If reduction precedes cyclization, the cyclization reaction proceeds rapidly, otherwise it ms desirable to add heat during cyclization.

A preferred solvent in which to carry out the reduction/cyclization reaction is isopropyl alcohol, although other solvents are suitable, such as other alcohols, tetrahydrofuran, esters, ethers, ketones and the like.

Cyctization is performed by contacting the hydrazone with a mild to strong base, such as sodium acetate, sodium bicarbonate, ammonium hydroxide, sodium hydroxide, triethylamine, diethylaniline, dimethylaniline, diazobicycloundecane, and the like. The cyclization reaction can proceed at a temperature in the range of 0° C. to 100° C., preferably 60° C. to 100° C.

The reduction step is performed preferably with a hydride reducing agent, such as sodium borohydride, a dialkyl aluminum hydride or lithium aluminum hydride at a temperature below 40° C; preferably between 0° C. and 30° C. When $R^1$ in Formula I is an alkyl group, it is preferred that reduction precede cyclization. The reaction mixture is then neutralized and the product collected by common techniques.

There is thus obtained an intermediate that can be used to prepare a wide variety of ballasted 1-H-pyrazolo[5,1-c]-1,2,4-triazole magenta dye forming couplers. To better prepare the intermediate for this use, it is preferred that the methine in the 3-position of the pyrazolotriazole be activated by attachment of an acyl group. A preferred procedure for accomplishing this is to first protect the nitrogen atom adjacent the 3-position carbon atom of the pyrazolotriazole ring by dichlorinating that carbon atom using a chlorinating agent, such as dichlorodimethyl hydantoin, sulfuryl chloride, or n-chlorosuccinimide, and then acylate the 3-position methine group with an acylating agent, such as acetic anhydride, followed by dechlorination with a reagent such as sodium dithionite, or ascorbic acid. These reactions can be carried out in water miscible organic solvents, such as methanol, ethanol, isopropanol, tetrahydrofuran, dioxane or acetonitrile, or as a 2-phase reaction mixture with an aqueous component and a solvent such as ethyl acetate or toluene as appropriate. Reaction temperatures are maintained below 40° C. The resulting intermediate can be collected by common techniques.

The following three schemes illustrate two preferred synthetic routes (Schemes I and II, which are part of the present invention) to the common intermediates and one route (Scheme III, which is not part of the present invention) that is less preferred because it uses a sulfur-containing reactant.

Scheme I illustrates the synthesis of the common intermediate example 2 (Table I) of the invention;

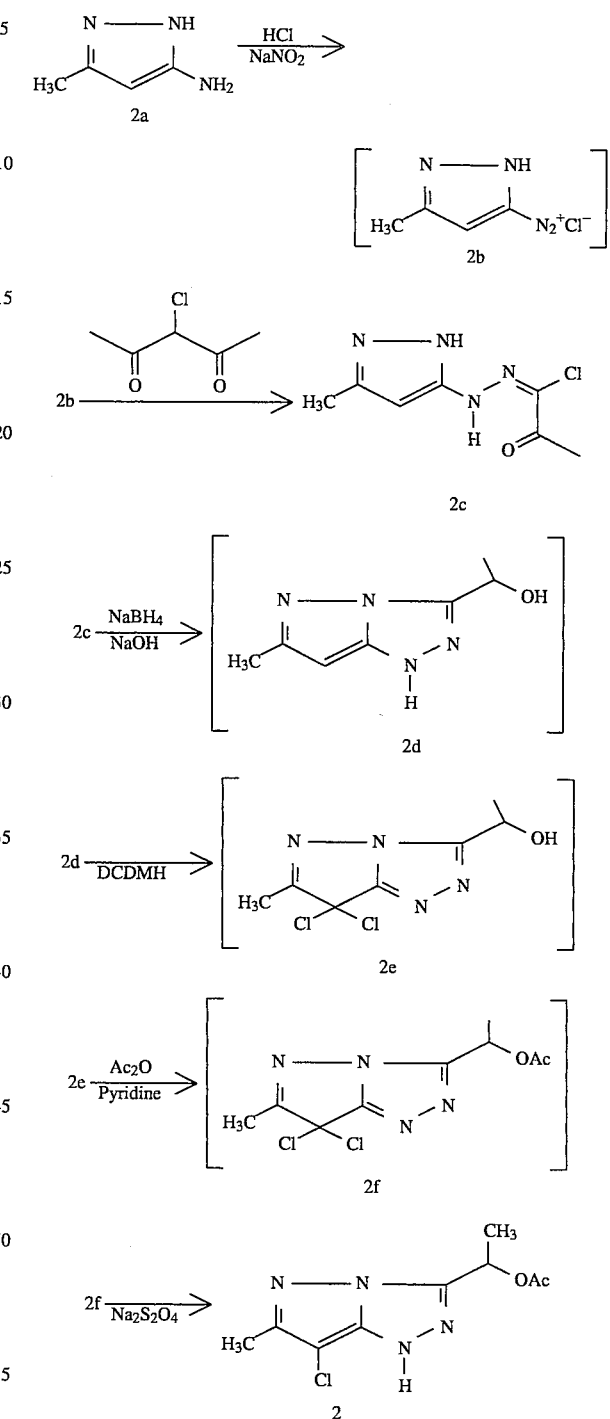

Diazotization of 5-amino-3-methyl-1H-pyrazole (2a) followed by Japp-Klingman reaction with an active methylene compound, 3-chloro-2,4-pentanedione, gives chlorohydrazone 2c which is converted to the pyrazolotriazole 2d through a reduction and ring closure reactions. Dichlorination of 2d with 1,3-dichloro-5,5-dimethylhydantoin (DCDMH) followed by acetylation and dechlorination give the common intermediate 2.

Scheme II illustrates the synthesis of the common intermediate example 18 (Table I) of the invention.

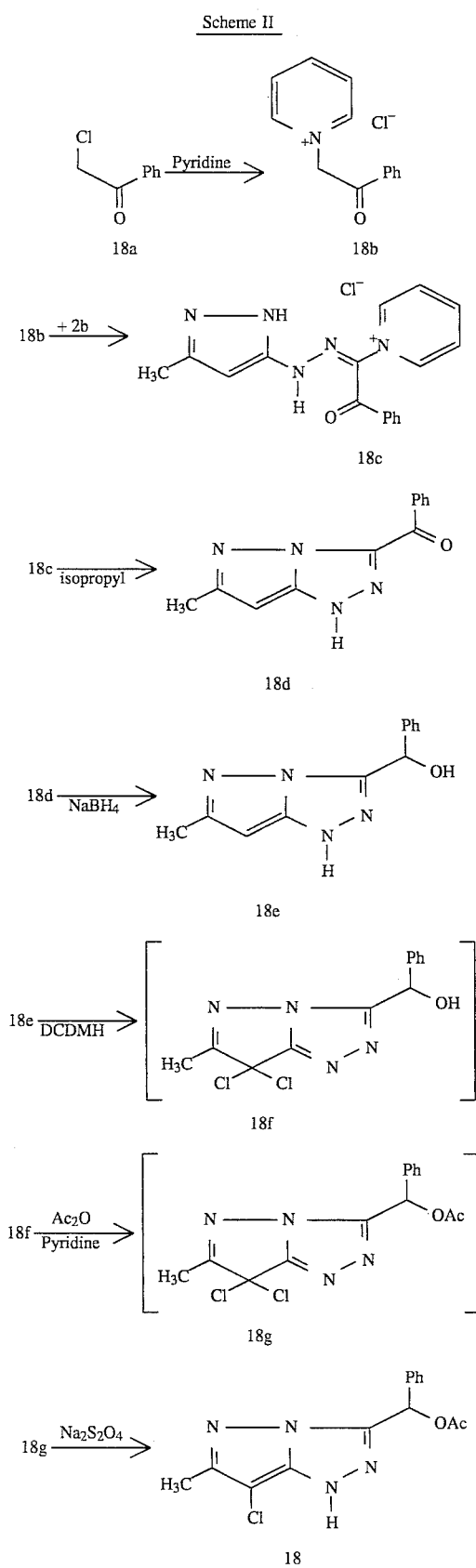

The synthetic sequence for Scheme II is similar to that for Scheme I. The difference is the use of 18b, 1-(2-oxophenylethyl)-pyridinium chloride, as the active methylene compound.

Scheme III illustrates the synthesis of the common intermediate example 3 of the invention;

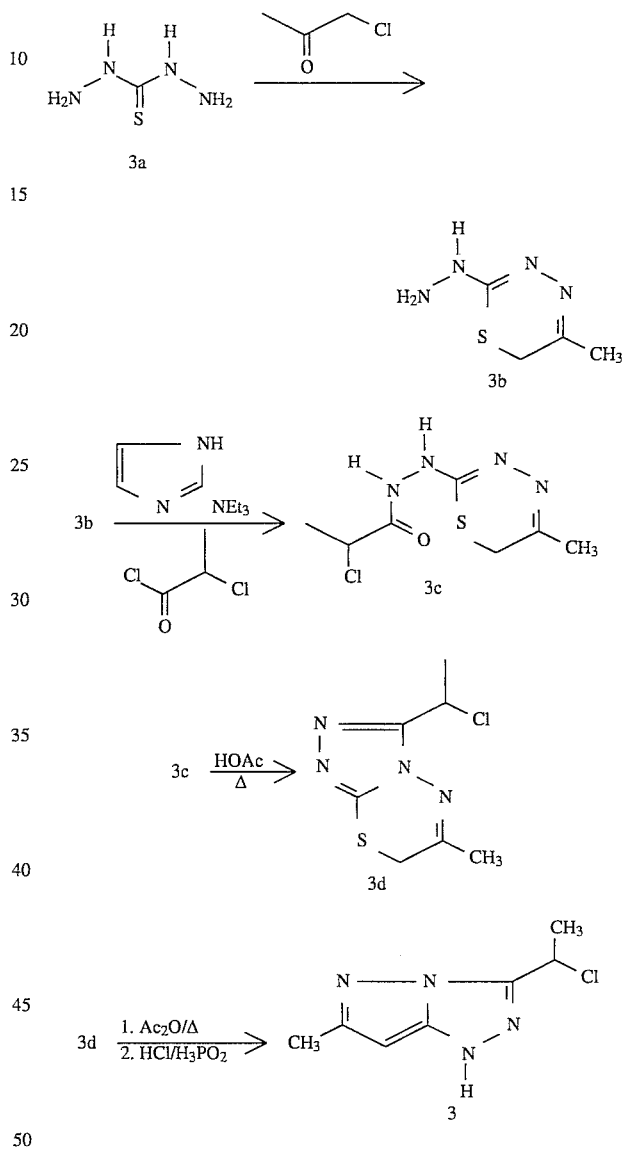

Acylation of hydrazinothiadiazine 3b with 2-chloropropionyl chloride followed by ring closure gives triaxolothiadiazine 3d. Ring contraction of 3d with acetic anhydride and subsequent reductive desulfurization give the desired pyrazolotriazole intermediate 3. This synthetic method is described in U.S. Pat. No. 5,055,586.

The common intermediates of this invention, including those listed in the Table I, can be synthesized by applying one of Schemes I or II shown above, or modifications of them known to those skilled in the art.

The following examples illustrate synthesis of representative intermediates of this invention. All compounds were characterized by spectral methods including mass spec, NMR, IR and/or combustion analysis.

Working Examples

1. Synthesis of Example 2
   Step 1 & 2

A solution of ·10.9 g sodium nitrite in 30 ml water is slowly added to a solution of 19.2 g 5-amino-3-methylpyrazole (2a) in 25 ml 12M HCl and 40 ml water. The reaction temperature is maintained below 5° C. using an ice bath. After stirring for 30 min, the diazonium salt (2b) solution is added to a solution of 20 g of 3-chloro-2,4-pentanedione in 30 ml isopropyl alcohol keeping the temperature at 15°–17° C. The reaction mixture is stirred at room temperature for 90 min and then a solution of 13 g sodium acetate in 40 ml water is added to the product slurry. The solids are collected, washed well with water, and dried to give 21 g (73% yield) of 2c. M/e=200, MP=165°–168° C., NMR, IR spectra were consistent with the reported structure.

Step 3-6

A solution of 3.1 g sodium borohydride in 12 ml 0.1N NaOH is added dropwise to a solution of 13.3 g 2c in 45 ml isopropyl alcohol and 15 ml methanol keeping the temperature below 35° C. The mixture is stirred for 1 hr and then 4 g acetone is added to destroy any excess borohydride. The solution is neutralized with 12M HCl, treated with carbon and magnesium sulfate, and filtered. To the filtrate, containing 2d, is added 13 g 1,3-dichloro-5,5-dimethylhydantoin (DCDMH) keeping the temperature under 40° C. The reaction mixture is stirred for 1 hr and then added to 130 ml water and 100 ml dichloromethane with vigorous stirring. The two phases are separated and the water layer is extracted twice with 100 ml each of dichloromethane. All dichloromethane extracts are combined, dried with magnesium sulfate, and filtered. The dichloromethane solution, containing intermediate 2e, is concentrated to half its original volume and 10.4 g pyridine, 0.3 g 4-N,N-dimethylaminopyridine (DMAP), and 26 g acetic anhydride are added, while keeping the temperature below 30° C. The reaction mixture is stirred for 1 hr and a solution of 13 g sodium dithionite in 70 ml water is added. The two phase reaction mixture is well stirred for 1 hr, then the phases are allowed to separate and the water layer is discarded. The organic layer is washed with 1M HCl and water, dried over magnesium sulfate, and filtered. The solution is concentrated to an oil under reduced pressure. The oil is crystalized from 20 ml toluene and 20 ml heptane. The solids are filtered, washed with cyclohexane, and dried to give 5.5 g (34% overall yield from 2c) of the common intermediate 2. The identity of 2 is confirmed by mp 110°–112° C., M/e=242, NMR, IR consistent with reported structure.

2. Synthesis of Example 18
   Step 1

Addition of 17.7 g pyridine is made to a solution of 33 g of phenacylchloride (18a) in 30 ml acetonitrile over a 10 min. period. The reaction mixture is stirred at room temperature for 1 hr after completion of the addition, and then slowly heated to 70° C. After 1 hr at 70° C., toluene (70 ml) is added to thin the thick reaction mixture. The slurry is cooled to 5° C. and the product is collected, washed, and dried to give 43.4 g (87% yield) of 18b. IR, NMR consistent with reported structure.

Step 2

The diazonium salt (2b) is prepared as described above in connection with the preparation of common intermediate example 2 from 12.5 g sodium nitrite and 15.1 g 2a. This solution is added to a stirred mixture of 35 g 18b in 80 ml isopropyl alcohol and 27 ml ammonium hydroxide, keeping the temperature at 15°–17° C. After stirring for 3 hrs at 15°–20° C., the solids are collected, washed with water, and dried to give 40.6 g (79% yield) of 18c. The identity of 18c is confirmed by IR, NMR consistent with reported structure.

Step 3

A mixture of 40 g 18c and 200 ml isopropyl alcohol is heated under reflux for 6 hrs. The mixture is cooled to 5° C. and kept at that temperature for 90 min. The product is collected and washed with isopropyl alcohol. The damp solids are slurried in 40 ml water for 30 min, collected, washed, and dried to give 21 g (79% yield) 18d. The identity of 18d is confirmed by IR, NMR consistent with reported structure.

Step 4

A solution of 2.4 g sodium borohydride in 10 ml 0.1N NaOH is added dropwise to a solution of 9 g of 18d in 90 ml isopropyl alcohol. The reaction temperature is maintained at 20°–30° C. during the addition, then the reaction mixture is stirred at 25° C. for 90 min. Acetone (4 g) is added and the mixture is neutralized with 6N HCl, then 90 ml acetonitrite is added and the product is collected. The damp solids are slurried in 200 ml water, collected and dried to give 17.4 g (91% yield) of 18e. The identity of 18e is confirmed by IR, NMR consistent with reported structure.

Step 5-7

To a solution of 15 g 18e in 100 ml ethyl acetate is added 12.9 g DCDMH. The mixture is stirred at room temperature for 1 hr, diluted with 80 ml tetrahydrofuran (THF) and 60 ml of ethyl acetate, and then 120 ml water (40° C.) is added with vigorous stirring. The phases are allowed to separate, the aqueous layer is extracted with additional ethyl acetate. The ethyl acetate liquors are combined, washed with water, dried over magnesium sulfate, and then concentrated to a thick residue. The residue is dissolved in 120 ml fresh ethyl acetate and 5.7 g pyridine, 0.3 g dimethylamino pyridine, and 7.4 g acetic anhydride are added. The reaction mixture is stirred at room temperature for 1 hr. A solution of 14.2 g sodium dithionite in 40 ml water is added and the mixture is well stirred at room temperature for an additional hour. The layers are allowed to separate and the ethyl acetate layer is washed with water, dried over magnesium sulfate, then concentrated to a thick residue. The solids are slurried in 60 ml cyclohexane, collected and dried to give 17.5 g (88% overall yield from 18e) of 18. The identity of 18 is confirmed by NMR, mass spectra and combustion analysis.

The common intermediates of the invention can be readily and efficiently converted to a wide variety of photographically useful magenta dye forming couplers. Substitution at the methine carbon in the side chain occurs through a replacement reaction of the leaving group Y and/or an elimination-addition process in which various nucleophiles, represented below as $HZR^2$ can participate to provide couplers represented below by the general structure (II).

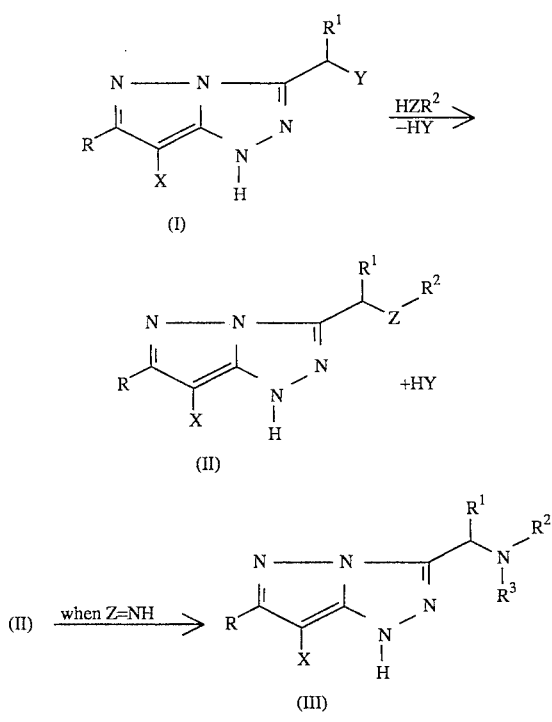

In the above structures Z represents O, S, $SO_2$, NH or $NR^1$ (where $R^1$ is an alkyl) and $R^2$ represents hydrogen, alkyl, aryl, aralkyl, cycloalkyl, heteroatkyl, heteroaryl, heterocyclic and similar groups found in the ballast group of a magenta dye forming coupler. When Z is NH, an additional group ($R^3$) can be attached as shown in general structure (III). $R^3$ represents acyl, alkylsuflonyl, S arysulfonyl, alkyl, or aralkyl.

In addition, certain coupling-off groups (e.g. Cl, Br, alkylsulfonyloxy, or arylsulfonyloxy) in the couplers of the types II or III can be replaced with other nucleophiles such as alkyl-, aryl-, or heteroaryl-mercaptan to give other couplers.

The replacement and elimination/addition reactions shown above to convert the common intermediate of this invention to a ballasted photographic dye forming coupler are known to those skilled in the coupler synthesis art. They are illustrated for example in U.S. Pat. No. 5,183,728.

A wide array of final coupler can be produced from the common intermediates of this invention. Tables II and III list examples of such couplers derived from four typical common intermediates (examples 2, 18, 25 and 28 from Table I above.)

TABLE II

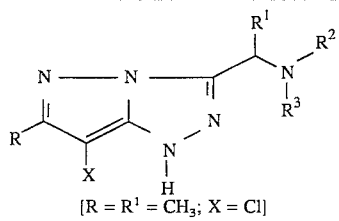

[R = $R^1$ = $CH_3$; X = Cl]

| Ex. No. | $R^2$ | $R^3$ |
|---|---|---|
| 2-1 | n-$C_{18}H_{37}$ | —$COCH_2(CH_2)_2CO_2H$ |
| 2-2 | n-$C_{18}H_{37}$ | (2-carboxycyclohexyl)carbonyl |
| 2-3 | n-$C_{18}H_{37}$ | 4-[(4-methylsulfonylamino)phenylsulfonylamino]benzoyl |

TABLE II-continued
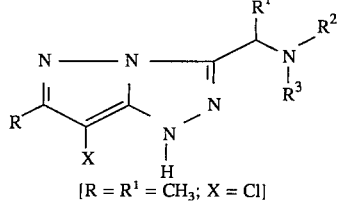
[R = R¹ = CH₃; X = Cl]
| Ex. No. | R² | R³ |
|---|---|---|
| 2-4 | n-C₁₈H₃₇ | 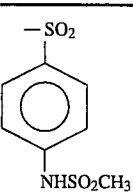 |
| 2-5 | n-C₄H₉ | 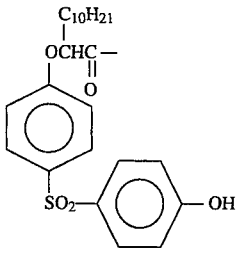 |
| 2-6 | 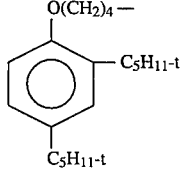 | —CO(CH₂)₂CO₂H |
| 2-7 | 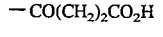 | —CO(CH₂)₂CO₂H |
| 2-9 | 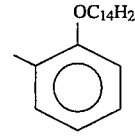 | 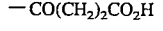 |

TABLE II-continued
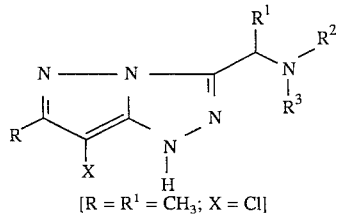
[R = R¹ = CH₃; X = Cl]
| Ex. No. | R² | R³ |
|---|---|---|
| 2-17 | 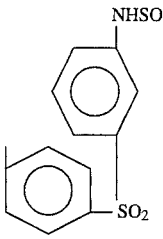 | —COC₁₅H₃₁ |
| 2-18 | 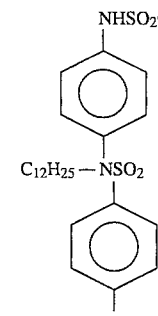 | —COC₅H₁₁ |
| 2-19 | 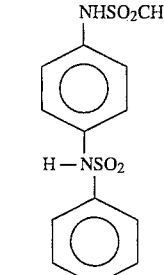 | —COC₁₇H₃₅ |
TABLE III
| Ex. No. | R² | R³ |
|---|---|---|
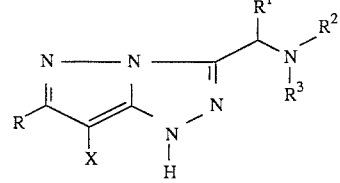
[R = CH₃; R¹ = Ph; X = Cl]
| Ex. No. | R² | R³ |
|---|---|---|
| 18-1 | n-C₁₈H₃₇ | —CO(CH₂)₂CO₂H |
TABLE III-continued
| Ex. No. | R² | R³ |
|---|---|---|
| 18-2 | n-C₁₈H₃₇ | 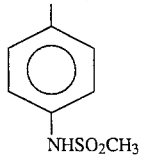 |
| 18-3 | n-C₁₈H₃₇ | 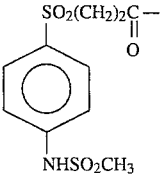 |

TABLE III-continued

| Ex. No. | R² | R³ |
|---|---|---|
| 18-4 | n-C₁₈H₃₇ | 4-(NHSO₂CH₃)-C₆H₄-SO₂NHCH₂C(=O)- |
| 18-5 | n-C₁₈H₃₇ | 4-(NHSO₂CH₃)-C₆H₄-CONHCH₂C(=O)- |
| 18-6 | n-C₁₈H₃₇ | 4-(NHSO₂CH₃)-C₆H₄-N(CH₃)C(=O)CH₂C(=O)- |
| 18-7 | n-C₁₈H₃₇ | 4-(NHSO₂CH₃)-C₆H₄-O(CH₂)₂C(=O)- |
| 18-8 | n-C₁₈H₃₇ | 4-(NHSO₂CH₃)-C₆H₄-O(CH₂)₃C(=O)- |
| 18-9 | n-C₁₈H₃₇ | 4-(NHSO₂CH₃)-C₆H₄-(CH₂)₃C(=O)- |
| 18-10 | n-C₁₈H₃₇ | 4-NO₂-C₆H₄-SO₂NH-C₆H₄-4-C(=O)- |
| 18-11 | n-C₄H₉ | 4-(NHSO₂CH₃)-C₆H₄-SO₂NH(CH₂)₁₀C(=O)- |
| 18-12 | n-C₄H₉ | 2-OH-C₆H₄ and 4-(SO₂-)-C₆H₄ fused structure with OCH(C₁₀H₂₁)C(=O)- [R = CH₃; R¹ = Ph; X = Cl] |
| 18-13 | —C₁₂H₂₅ | 4-(NHSO₂CH₃)-C₆H₄-C(=O)- |
| 18-14 | —(CH₂)₃OC₁₂H₂₅ | 4-(NHSO₂CH₃)-C₆H₄-C(=O)- |
| 18-20 | 4-(NHSO₂CH₃)-C₆H₄-SO₂-C₆H₄- | —COC₁₅H₃₁ |
| 18-21 | 4-(NHSO₂CH₃)-C₆H₄-N(C₁₂H₂₅)SO₂-C₆H₄- (fused) | —COC₅H₁₁ |
| 18-24 | 2,4-di-(t-C₅H₁₁)-C₆H₃-O(CH₂)₄- | —CO(CH₂)₂CO₂H |

[R = CH₃; R¹ = Ph; X = —O—C₆H₄—SO₂CH₃]

| 25-1 | n-C₁₈H₃₇ | —CO(CH₂)₂CO₂H |

TABLE III-continued
| Ex. No. | R² | R³ |
|---|---|---|
| 25-2 | n-C₁₈H₃₇ | —SO₂—C₆H₄—NHSO₂CH₃ |
| 25-3 | n-C₄H₉ | C₁₀H₂₁OCHC(=O)—C₆H₄—SO₂—C₆H₃(OH)— |
| 25-4 | 2,4-di-t-C₅H₁₁-C₆H₃-O(CH₂)₄— | —CO(CH₂)₂CO₂H |
[ R = CH₃; R¹ = Ph; X = —N-pyrazolyl ]
TABLE III-continued
| Ex. No. | R² | R³ |
|---|---|---|
| 28-1 | —C₁₂H₂₅ | —C(=O)—C₆H₄—NHSO₂CH₃ |
| 28-2 | —(CH₂)₃OC₁₂H₂₅ | —C(=O)—C₆H₄—NHSO₂CH₃ |
EXPERIMENTAL
Working Examples
3. Synthesis of Example 2-6
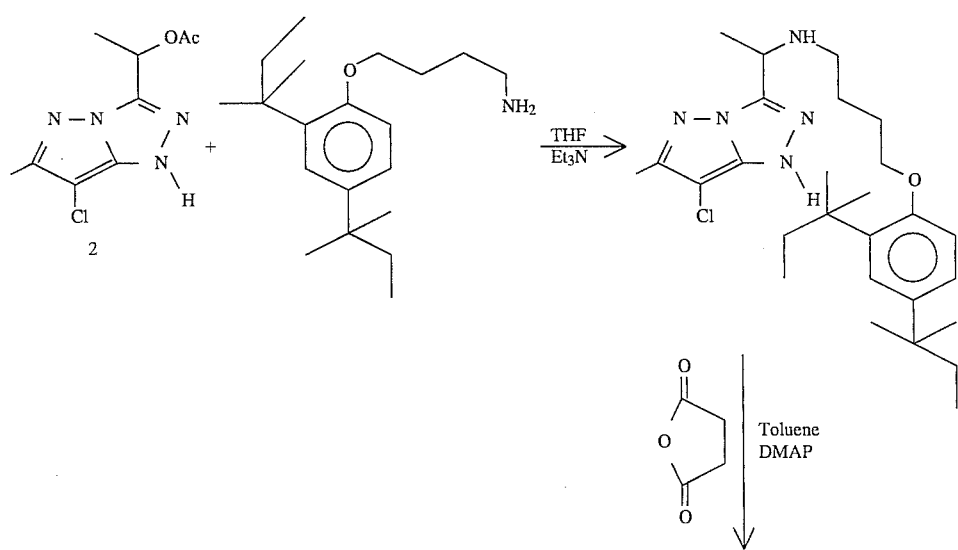

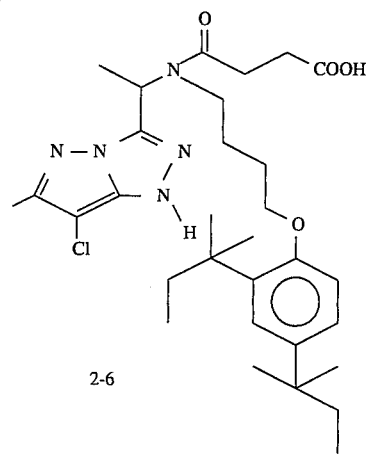

20

To a stirred solution of 2 (4.84 g, 0.02 mol) in tetrahydrofuran (60 mL) was added 4-[2,4-bis(1,1-dimethylpropyl)phenoxy] -1-butanamine (6.11 g, 0.02 mol) followed by triethylamine (2.02 g, 0.02 mol). The resulting mixture was heated at reflux for 1 h. It was then cooled to ambient temperature and then stripped to an oil by rotary evaporation. The oil was dissolved in ethyl acetate and washed successively with water, brine, dried over MgSO$_4$, filtered and concentrated to an oil which was chromatographed on silica gel (elution with 3:1 ethyl acetate:hexanes, then 1:1:1 ethyl acetate:methylene chloride:hexanes) to provide 6.92 g (71%) of a viscous oil.

The oily product (9.0 g, 0.018 mol) was dissolved in toluene (150 mL) and to it was added succinic anhydride (1.84 g, 0.018 mol) followed by N'N-dimethylamino pyridine (200 mg). The mixture was heated to reflux and stirred for 0.5 h at reflux. It was then cooled, stripped to an oil and chromatographed on silica gel (elution with 5% methanol in methylene chloride) to provide an oil which was crystallized from acetonitrile to yield 8.25 g (78.6%) of 2-6 as fine off-white crystals, mp=150°–152° C., M/e=587, anal. calcd. for $C_{31}H_{46}ClN_5O_4$: C, 63.30%; H, 7.88%; N, 11.91%; found: C, 63.41%; H, 7.88%; N, 11.71%. NMR and IR spectra were consistent with the reported structure.

4. Synthesis of Example 18-1

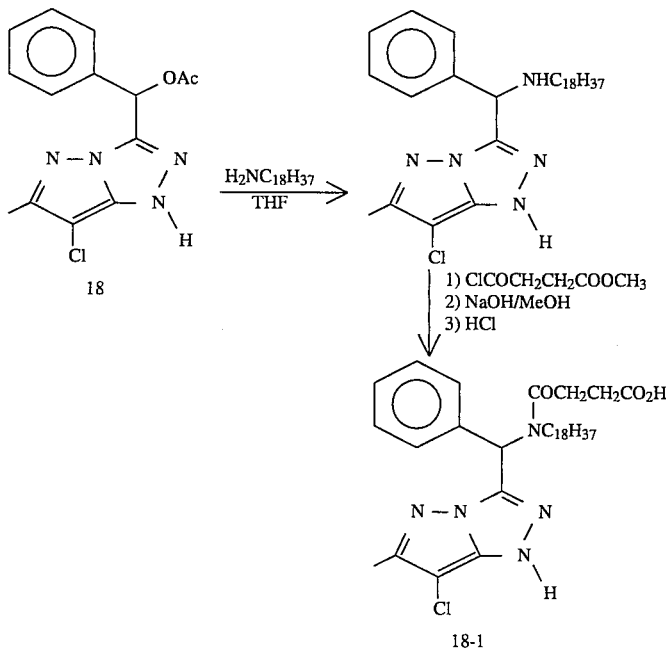

To a stirred solution of 35 g 18 in 1000 ml THF is added 40.6 g octadecyl amine and the resulting mixture is heated under reflux for 13 hrs. The solvent is removed under vacuum and the residue is dissolved in dichlormethane and passed through a thick pad of silica gel (eluted with 5% up to 20% ethyl acetate in dichloromethane). The product containing fractions are concentrated under vacuum. The residue is triturated with acetonitrile, collected, and dried to give 59 g of tan solids.

To a stirred solution of the above solids and 29 g of N,N-dimethylaniline in 500 ml THF is added 28.5 g of 3-methoxycarbonylpropionyl chloride and the resulting mixture is stirred for 3 hrs. Methanol (300 ml) is added followed by a solution of 50 g NaOH in 300 ml water and the mixture is stirred for an additional hour. The product is extracted with 2000 ml ethyl acetate and the ethyl acetate solution is washed with 5% HCl and brine, dried over magnesium sulfate, filtered and concentrated to an oil. The oil is dissolved in dichloromethane containing 1% acetic acid and chromatographed on a thick pad of silica gel (eluted with 5% to 20% ether in dichloromethane). The product containing fractions are concentrated to provide solids which are triturated with 400 ml acetonitrile, filtered, and dried to give 53.5 (75%) of 18-1.

5. Synthesis of Example 18-2

A solution of 115 g 18 and 107 g n-octadecyl amine in 1.15 liter of tetrahydrofuran (THF) is heated to reflux for 10 minutes only (longer heating leads to byproducts). The dark purple solution is concentrated to an oil under reduced pressure. The oil solidifies upon treatment with 1.15 liter of acetonitrile and stirring for 4 hour. The solids are filtered, washed with acetonitrile until washings are no longer dark and dried to give 188 g (97% yield) of 3.

105 g of the acid chloride 4 is added to a solution of 155 g ! and 114 ml of dimethylaniline in 1.0 liter of tetrahydrofuran (THP). The mixture is stirred at ambient temperature for 16 hr. Filtered off and discarded a small amount of insolubles through a short pad of celite. The filtrate is diluted with 2.0 liter of ethyl acetate and washed with 2.0 liter of 1.0 normal HCl, 2×1.0 liter of saturated sodium bicarbonate solution, 2×500 ml 1.0 normal HCl and once with 500 ml brine. The organic product layer is dried over magnesium sulfate and concentrated to an oil under reduced pressure. Chromatography through silica gel yielded 94 g of solids upon concentration under reduced pressure. Crystalization from 700 ml acetonitrile yielded 90 g (42%) of 18-2 as a white solid (m.p.=138°–140° C.). The structure of 18-2 was confirmed by elemental analysis, NMR and mass spectrometry.

The invention has been described with reference to specific embodiments. It will be appreciated by those skilled in the art that modifications can be made within the spirit and scope of the invention.

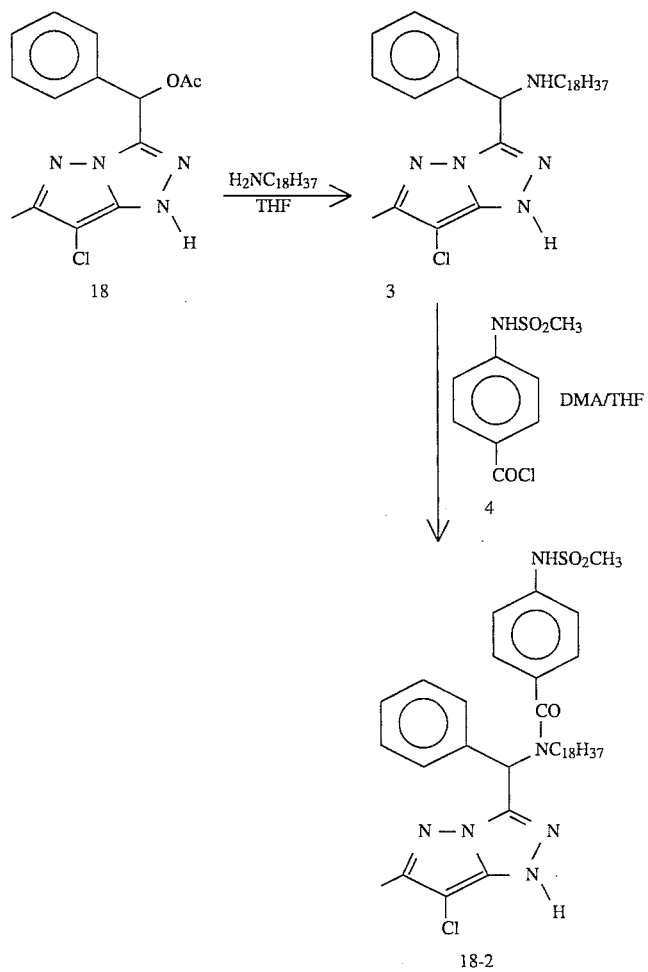

What is claimed is:
1. A process for synthesizing an intermediate for use in the preparation of a magenta dye forming coupler, the interme- diate being a 1H-pyrazolo[5,1-c][1,2,4]triazole compound having the structure,

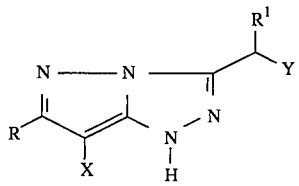

wherein:
R is an alkyl, acyl, aryl or heterocyclic group, linked to the ring directly or through a hetero atom;
X is hydrogen, a precursor of a coupling-off group, or a coupling-off group;
$R^1$ is hydrogen, or an alkyl, aryl or heterocyclyl group; and
Y is a leaving group which is replaceable by a nucleophilic replacement or an elimination/addition reaction, the process comprising the steps of:
(1) diazotizing a 5-amino-1H-pyrazole in the presence of an acidic nitrite salt or ester to produce a 5-diazo-1H-pyrazole;
(2) condensing the diazotized product in the presence of an active methine or methylene compound having a pKa of 14 or less to produce a substituted hydrazone compound;
(3) subjecting the hydrazone product to cyclization and reduction, in either order, to produce an intermediate compound having the above structure.

* * * * *